(12) United States Patent
Thastrup et al.

(10) Patent No.: US 6,566,083 B1
(45) Date of Patent: *May 20, 2003

(54) METHOD OF DETECTING BIOLOGICALLY ACTIVE SUBSTANCES

(75) Inventors: Ole Thastrup, Birkerød; Søren Tullin, Søborg; Lars Kongsbak Poulsen, Holte; Sara Petersen Bjørn, Lyngby, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/346,946

(22) Filed: Jul. 2, 1999

Related U.S. Application Data

(63) Continuation of application No. 08/818,604, filed on Mar. 14, 1997, now Pat. No. 5,958,713, which is a continuation of application No. PCT/DK96/00052, filed on Jan. 31, 1996.

(30) Foreign Application Priority Data

Jan. 31, 1995 (DK) ................................ 0110/95
Sep. 7, 1995 (DK) ................................ 0982/95

(51) Int. Cl.⁷ ............................................ G01N 33/573
(52) U.S. Cl. .......................... 435/7.4; 435/7.4; 435/7.2; 435/6; 435/7; 435/69.1; 435/320.1; 435/235.1; 530/387.1; 530/350; 530/300; 536/23.1
(58) Field of Search .......................... 435/7.2, 7, 69.1, 435/320.1, 235.1; 536/23.1; 530/387.1, 350, 300

(56) References Cited

U.S. PATENT DOCUMENTS 5,958,713 A * 9/1999 Thastrup et al. ............. 435/7.4

FOREIGN PATENT DOCUMENTS

| WO | WO 91/01305 | * | 2/1991 |
| WO | WO 95/07463 | | 3/1995 |
| WO | WO 95/21191 | | 8/1995 |

OTHER PUBLICATIONS

Martin Chalfie et al., "Green Fluorescent Protein . . . " Science, vol. 263, Feb. 11, 1994 . . . pp. 802–803.
Sala–Newby et al., "Engineering a bioluminescent indicator . . . " Biochemcial Journal vol. 279, pp. 727–732.
Sala–Newby et al. "Engineering firefly luciferase . . . " FEBS letters vol. 307, No. 2, pp. 241–244.
Sala–Newby et al. "Engineering protein kinase recognition . . . " Biolumin. Chemilumin. Proc. Int. Symp. Stanely et a., eds. Wiley, UK, pp. 23–26.
Campbell et al. "Engineering bioluminescent proteins . . . " Methodol. Surv. Biochem. Anal. vol. 21, pp. 311–316.

* cited by examiner

Primary Examiner—Karen Cochrane Carlson
Assistant Examiner—Sheridan Sredden
(74) Attorney, Agent, or Firm—Birch, Stewart, Kolasch & Birch, LLP

(57) ABSTRACT

The present invention relates to a method of detecting biologically active substances affecting intracellular processes, an isolated DNA, a vector and a cell for use in the method. More specifically, the present invention provides a method for detecting a biologically active substance that affects intracellular processes mediated through a protein kinase or a second messenger, which comprises incubating a cell with a test substance and measuring any change caused by the test substance in the flourescence of (i) a wild-type or modified green flourescent protein (GFP) having a protein kinase recognition site, (ii) a modified GFP containing a second messenger binding domain, or (iii) a hybrid polypeptide having a wild-type or modified GFP and an attached protein kinase recognition site or a second messenger binding domain.

33 Claims, 6 Drawing Sheets

NUCLEOTIDE SEQUENCE (764 bp) OF GFP
(Hind3 - EcoRI FRAGMENT)

```
AAGCTTTATGAGTAAAGGAGAAGAACTTTTCACTGGAGTT
GTCCCAATTCTTGTTGAATTAGATGGCGATGTTAATGGGC
AAAAATTCTCTGTTAGTGGAGAGGGTGAAGGTGATGCAAC
ATACGGAAAACTTACCCTTAAATTTATTTGCACTACTGGG
AAGCTACCTGTTCCATGGCCAACGCTTGTCACTACTTTCT
CTTATGGTGTTCAATGCTTTTCAAGATACCCAGATCATAT
GAAACAGCATGACTTTTTCAAGAGTGCCATGCCCGAAGGT
TATGTACAGGAAAGAACTATATTTTACAAAGATGACGGGA
ACTACAAGACACGTGCTGAAGTCAAGTTTGAAGGTGATAC
CCTTGTTAATAGAATCGAGTTAAAAGGTATTGATTTTAAA
GAAGATGGAAACATTCTTGGACACAAATGGAATACAACT
ATAACTCACATAATGTATACATCATGGCAGACAAACCAAA
GAATGGCATCAAAGTTAACTTCAAAATTAGACACAACATT
AAAGATGGAAGCGTTCAATTAGCAGACCATTATCAACAAA
ATACTCCAATTGGCGATGGCCCTGTCCTTTTACCAGACAA
CCATTACCTGTCCACGCAATCTGCCCTTTCCAAAGATCCC
AACGAAAAGAGAGATCACATGATCCTTCTTGAGTTTGTAA
CAGCTGCTGGGATTACACATGGCATGGATGAACTATACAA
ATAAATGTCCAGACTTCCAATTGACACTAAAGGGATCCGA
ATTC
```

FIG. 4A

AMINO ACID SEQUENCE:

START CODON ATG CORRESPONDS TO POSITION 8 IN THE NUCLEOTIDE SEQUENCE ABOVE AND STOP CODON TAA
CORRESPONDS TO POSITION 722.

```
1/1                                                      31/11
atg agt aaa gga gaa gaa ctt ttc act gga gtt gtc cca att ctt gtt gaa tta gat ggc
Met ser lys gly glu glu leu phe thr gly val val pro ile leu val glu leu asp gly 61/21                                                    91/31
gat gtt aat ggg caa aaa ttc tct gtt agt gga gag ggt gaa ggt gat gca aca tac gga
asp val asn gly gln lys phe ser val ser gly glu gly glu gly asp ala thr tyr gly 211/71
181/61
aaa ctt acc ctt aaa ttt att tgc act act ggg aag cta cct gtt cca tgg cca acg ctt
lys leu thr leu lys phe ile cys thr thr gly lys leu pro val pro trp pro thr leu 121/41                                                   151/51
gtc act act ttc tct tat ggt gtt caa tgc ttt tca aga tac cca gat cat atg aaa cag
val thr thr phe ser tyr gly val gln cys phe ser arg tyr pro asp his met lys gln 241/81                                                   271/91
cat gac ttt ttc aag agt gcc atg ccc gaa ggt tat gta cag gaa aga act ata ttt tac
his asp phe phe lys ser ala met pro glu gly tyr val gln glu arg thr ile phe tyr
```

FIG. 4B-1

```
301/101
aaa gat gac ggg aac tac aag aca cgt gct gaa gtc aag ttt gaa ggt gat acc ctt gtt
lys asp asp gly asn tyr lys thr arg ala glu val lys phe glu gly asp thr leu val
                                              331/111
361/121
aat aga atc gag tta aaa ggt att gat ttt aaa gaa gat gga aac att ctt gga cac aaa
asn arg ile glu leu lys gly ile asp phe lys glu asp gly asn ile leu gly his lys
                                              391/131
421/141
atg gaa tac aac tat aac tca cat aat gta tac atc atg gca gac aaa cca aag aat ggc
met glu tyr asn tyr asn ser his asn val tyr ile met ala asp lys pro lys asn gly
                                              451/151
481/161
atc aaa gtt aac ttc aaa att aga cac aac att ggc gat gga agc gtt caa tta gca gac
ile lys val asn phe lys ile arg his asn ile gly asp gly ser val gln leu ala asp
                                              511/171
541/181
cat tat caa caa aat act cca att ggc gat ggc cct gtc ctt tta cca gac aac cat tac
his tyr gln gln asn thr pro ile gly asp gly pro val leu leu pro asp asn his tyr
                                              571/191
601/201
ctg tcc acg caa tct gcc ctt tcc aaa gat ccc aac gaa aag aga gat cac atg atc ctt
leu ser thr gln ser ala leu ser lys asp pro asn glu lys arg asp his met ile leu
                                              631/211
661/221
ctt gag ttt gta aca gct gct ggg att aca ggc atg gat gaa cta tac aaa taa
leu glu phe val thr ala ala gly ile thr gly met asp glu leu tyr lys OCH
                                              691/231
```

METHOD OF DETECTING BIOLOGICALLY ACTIVE SUBSTANCES

CROSS-REFERENCE TO RELATED APPLICATIONS

This application is a continuation of U.S. patent application Ser. No. 08/818,604, filed Mar. 14, 1997, which has matured into U.S. Pat. No. 5,958,713, which in turn is a continuation of PCT/DK96/00052 filed Jan. 31, 1996, which claims priority to Danish application serial nos. 0110/95 and 0982/95 filed Jan. 31, 1995 and Sep. 7, 1995, respectively, the contents of each of which are incorporated herein by reference.

FIELD OF INVENTION

The present invention relates to a method of detecting biologically active substances affecting intracellular processes, and a DNA construct and a cell for use in the method.

BACKGROUND OF THE INVENTION

Second messengers and protein kinases play key roles in the signalling pathways that control the response of mammalian cells (and probably all eukaryotic cells) to most stimuli. Although such signalling pathways have been subjected to extensive studies, detailed knowledge on e.g. the exact timing and spatial characteristics of signalling events is often difficult to obtain due to lack of a convenient technology. There is, however, one exception to this rule: our understanding of the role of $Ca^{2+}$ in e.g. intracellular signalling has been greatly improved due to the development of the fluorescent $Ca^{2+}$ probe FURA-2 that permits real times studies of $Ca^{2+}$ in single living cells.

Moreover, the construction of probes of cAMP (Adams et al., Nature 349 (1991), 694–697) and activity of the cAMP-dependent protein kinase (Sala-Newby and Campbell, FEBS 307(2) (1992), 241–244) has been attempted. The protein kinase A probe, however, suffers from the drawback that it is based on the firefly luciferase and accordingly produces too little light for fast single cell mesurements. The cAMP probe on the other hand has to be microinjected and is therefore not well suited for routine laboratoy work.In conclusion, both probes lack some of the elegant properties that resulted in the widespread use of FURA-2.

Recently it was discovered that Green Fluorescent Protein (GFP) expressed in many different cell types, including mammalian cells, becam highly flourescent (Chalfie et al., Science 263 (1994), 802–805). WO/07463 describes a cell capable of expressing GFP and a method for selecting cells expressing a protein of interest and GFP based on detection of GFP-flourescence in the cells.

SUMMARY OF THE INVENTION

The purpose of the present invention is to provide a method of detecting a biologically active substance affecting intracellular processes based on the use of green fluorescent protein, including wild-type GFP derived from the jelly fish *Aequorea victoria* and modifications of GFP, such as modifications that changes the spectral properties of the GFP fluorscence, for the construction of probes, preferably real time probes for second messengers and protein kinase activity.

In one aspect, the present invention relates a DNA construct comprising a DNA sequence coding for (i) green fluorescent protein (GFP) wherein one or more amino acids have been substituted, inserted or deleted to provide a binding domain of a second messenger or an enzyme recognition site, or (ii) a hybrid polypeptide of green fluorscent protein (GFP) or a modified GFP and a binding domain of a second messenger or an enzyme recognition site.

In another aspect, the present invention relates to a cell containing a DNA sequence coding for (i) green fluorscent protein wherein one or more amino acids have been substituted, inserted or deleted to provide a binding domain of a second messenger or an enzyme recognition side, or (ii) a hybrid polypeptide of green fluorescent protein (GFP) or a modified GFP and a binding domain of a second messenger or an enzyme recognition site, and capable of expressing said DNA sequence.

In a further aspect, the present invention relates to a method of a detecting a biologically active substance affecting intracellular processes,the method comprising (a) culturing a cell containing a DNA sequence coding for
  (i) green fluorscent protein wherein one or more amino acids have been substituted, inserted or deleted to provide a binding domain of a second messenger or an enzyme recognition site, or
  (ii) a hybrid polypeptide of green flourscent protein (GFP) or a modified GFP and a binding domain of a second messenger or an enzyme reognition site under conditions permitting expression of DNA sequence, (b) measuring the flourscence of the cell, (c) incubating the cell with a sample suspected of containing a biologically active substance affecting intracellular processes, and (d) measuring the fluorescence produced by the incubated cell and determining any change in the fluorescence compared to the fluorscence measured in step (b), such change being indicative of the prescence of a biologically active substance in said sample.

In a still further aspect, the present invention relates to a method of characterizing the biological activity of a substance with biological activity, the method comprising (a) culturing a cell containing a DNA sequence coding for
  (i) green fluorescent protein wherein one or more amino acids have been substituted, inserted or deleted to provide a binding domain of a second messenger or an enzyme recognition site or
  (ii) a hybrid polypeptide of green fluorescent protein (GFP) or a modified GFP and a binding domain of a second messenger or an enzyme recognition site under conditions permitting expression of DNA sequence, (b) measuring the fluorescence of the cell, (c) incubating the cell with a sample of a biologically active substance affecting intracellular processes, and (d) measuring the fluorescence produced by the incubated cell and determining any change in the fluorescence compared to the fluorscence measured in step (b), said change being characteristic of the biological activity of the biologically active substance in said sample.

Furthermore, studies on the substrate specificity of the different protein kinase A (PKA) isoforms using synthetic peptides have shown that peptides contianing the motifs RRXSX (SEQ ID NO: 33) or RXKRXXSX (SEQ ID NO: 34) (S being the phosphorylated amino acid) tend to be the best substrates for PKA, and a review by Zetterquist, Ö, et al. (in Kemp, B. E. (ed). Peptide and Protein Phosphorylation (1990), 172–188, CRC Press, Boca Raton, Fla., U.S.A.) confirms that most known substrates of PKA contain said motifs.

Available amino acid sequences of GFP do not suggest that GFP is a PKA substrate because of a lack of recognition sites comprising the motifs RRXSX (SEQ ID NO: 33) OR RXKRXXSX (SEQ ID NO: 34). It is therefore surprising that a native or wild-type green fluorescent protein (GFP) derived from the jellyfish *Aequorea victoria* can be phosphorylated by protein kinase A and thereby the spectral properties of GFP are changed resulting in a substantial increase of fluorescence.

In a preferred aspect, the present invention relates to a method of detecting a biologically active substance affecting intracellular processes, the method comprising (a) culturing a cell containing a DNA sequence coding for a wild-type green fluorescent protein having a protein kinase recognition site under conditions permitting expression of the DNA sequence, (b) measuring the fluorescence of the cell, (c) incubating the cell with a sample suspected of containing a biologically active substance affecting intracellular processes, and (d) measuring the fluorescence produced by the incubated cell and determining any change in the fluorescence compared to the fluorescence measured in step (b), such change being indicative of the presence of a biologically active substance in said sample.

In a further preferred aspect, the present invention relates to a method of characterizing the biological activity of a substance with biological activity, the method comprising (a) culturing a cell containing a DNA sequence coding for a wild-type green fluorescent protein having a protein kinase recognition site, under conditions permitting expression of the DNA sequence.

(b) measuring the flourescence of the cell, (c) incubating the cell with a sample of a biologically active substance affecting intracellular processes, and (d) measuring the flourescence produced by the incubated cell and determining any change in the flourescence compared to the flourescence measured in step (b), said change being characteristic of the biological activity of the biologically active substance in said sample.

In a still further preferred aspect the present invention relates to DNA construct comprising the DNA sequence shown in FIG. 4a, SEQ ID NO: 30, coding for a wild-type GFP an a transformed cell containing said DNA construct and capable of expressing said DNA sequence. The transformed cell is preferably a mammalian cell. A microorganisam *Echerichia coli* NN049087, carrying the DNA sequence shown in FIG. 4a has been deposited for the prupose of patent procedure according to the Budapest Treaty in the Deutsche Sammlung von Microganismen und Zellkulturen Gmbh, Mascheroderweg 1 b, D-38124 Braunschweig, Germany, under the deposition No. DSM 10260 on Sep. 21, 1995.

In the present context, the term "green fluorescent protein" is intended to indicate a protein which, when expressed by a cell, emits fluorscence (cf. Chalfie et al., *Science* 263, 1994, pp. 802–805). In the following, GFP in which one or more amino acids have been substituted, inserted or deleted is most often termed "modified GFP".

The term "second messenger" is used to indicate a low molecular weight component invloved in the early events of intracellular signal transduction pathways.

The term "binding domain of a second messenger" is used to indicate a segment of a protein which, in the course of intracellular metabolic proceses, binds the secondary messenger.

The term "enzyme recognition site" is intended to indicate a peptide sequence covalently modified by a enzyme (e.g. phosphorylated, glycosylated or cleaved), preferably the enzyme recognition site is a protein kniase recognition site, which is intended to indicate a peptide sequence covalently modified by a kniase, i.e. phosphorylated.

It should be emphasized that phosphorylation of a protein at a protein kinase recognition site often is followed (or accompanied) by dephosphorylation of said protein. A GFP based probe for activity of given protein kinase(s) would therefore also provide information on the activity of relevant protein phosphatases since the parameter monitored is the net phosphorylation of GFP based probe.

The term "hybrid polypeptide" is intended to indicate a polypeptide which is a fusion of at least a portion of each of two proteins, in this case at least a portion of the green fluorescent protein and at least a portion of a binding domain of a second messenger or an enzyme recognition site.

In the present context, the term "biologically active substance" is intended to indicate a substance which has a biological function or exerts a biological effect in the human or animal body. The sample may be a sample of a biological material such as a microbial extract, or it may be a sample containing a compound or mixture of compounds prepared by organic synthesis.

The phrase "any change in fluorescence" means any change in absorption properties, such as wavelength an intensity, or any change in spectral properties of the emitted light, such as a change of wavelength, fluorescence lifetime, intensity or polarisation.

The mechanism(s) behind a change in e.g. the fluorescence intensity of a modified GFP upon phosphorylation could be several. As one possibility, phosphorylation of said GFP variant could change the chromophore environment, either due to proximity of the added phosphate group or to phosphorylation induced conformation changes. Correspondingly, binding of e.g. a second messenger to the binding domain of a some GFP variant or GFP fusion protein couild induce conformational changes that ultimately changes the chromophore environment and thereby the fluorescence. As support for these suggestions, it has been shown that amino acid substitutions distant to the chromophore (e.g. amino acids 167, 202, 203 and 222) can change the fluorescence intensity and spectral characteristics of GFP (Ehrig et al. (1995) *FEBS Letters* 367:163; Heim et al.(1994) *Proc. Natl. Acad. Sci*, 91:12501).

The development of luminescent probes according to the present invention allows real time studies of second messengers and specific enzymes such as protein kinases in single living cells, thereby making it possible to study the precise timing and the spatial characteristics of these factors. Moreover, studies on heterogeneity in cell populations are made possible.

Due to the strong fluorescence of GFP, the luminescence of cells expressing the probes may easily be detected and analyzed by employing a combination of fluorescence microscopy and image analysis. Furthermore, it should be emphasized that the probes described are easy to introduce into cells, as they can be expressed in the cells of interest after transfection with a suitable expression vector.

Real time recombinant probes for second messengers and enzyme activity, such as kinase activity, are not only useful in basic research but also in screening programmes aiming at identifying novel biologically active substances. Many currently used screening programmes designed to find compounds that affect cAMP concentration and protein kinase activity are based on receptor binding and/or reporter gene expression. The recombinant probes described herein, on the other hand, make it possible to develop an entirely new type of screening assays able to monitor immediate and transient changes of cAMP concentration and protein kinase activity in intact living cells.

Any novel feature or combination of features described herein in considered essential to this invention.

BRIEF DESCRIPTION OF THE DRAWINGS

The invention is further illustrated in the following examples with reference to the appended drawings, wherein

FIG. 4a shows the DNA sequence (SEQ ID NO: 30) coding for a wild-type GFP (Hind3-EcoR1 fragment).

FIG. 4b shows the amino acid sequence (SEQ ID NO: 32), wherein start codon ATG corresponds to position 8 and stop codon TAA corresponds to position 722 in the nucleotide sequence of FIG. 4a.

Figure 1:
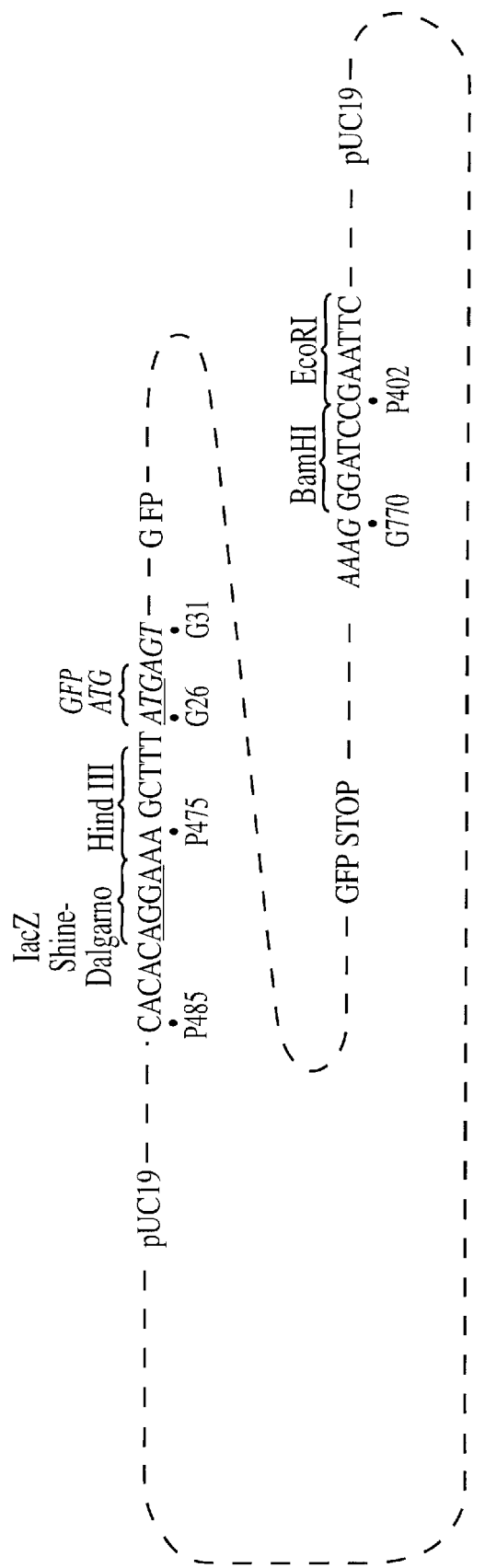
FIG. 1 shows a map of the pUC19-GFP plasmid construction. GFP nucleotide numbers referred to below with a "G" are from the GenBank GFP sequence record (accession No. M62653). Bases in italics represent GFP sequence. The pUC19 nucleotide numbers referred to below with a "P" are from the GenBank pUC19 sequence record (accession No. X02514). Bases in plain text represent pUC19 sequence. Bases in bold represent non-GFP non-pUC19 sequence (SEQ ID NOS: 27 and 28), which have been inserted by PCR for the introduction convenient restriction sites.

GFP nucleotide numbers referred to below with a "G" are from the GenBank GFP sequence record (accession No. M62653). CRP nucleotide numbers referred to below with a "C" are from the GenBank CRP sequence record (accession No. M13770). The pUC19 nucleotide numbers referred to below with a "P" are from the GenBank pUC19 sequence record (accession No. X02514).

DETAILED DESCRIPTION OF THE INVENTION

In a preferred embodiment of the present invention, the gene encoding GFP is derived from the jellyfish *Aequorea victoria*. The sequence of this gene is described in Prasher et al., *Gene* 111, 1992, pp. 229–233 (GenBank Accession No. M62653). The gene may be modified so as to code for a variant GFP in which one or more amino acid residues have been substituted, inserted or deleted to provide a binding domain of a second messenger or an enzyme recognition site. According to this embodiment, it is preferred to insert a DNA sequence coding for an enzyme recognition site into the gene coding for GFP, for instance at one of the following positions: between amino acid 39 and 40, between amino acid 71 and 72, between amino acid 79 and 80, between amino acid 107 and 108, between amino acid 129 and 130, between amino acid 164 and 165, or between amino acid 214 and 125. Points of insertion may be selected on the basis of surface probability (which may be calculated using the GCG software package which employs formula of Emini et al., *J. Virol,* 55(3), 1985, pp. 836–839). When the enzyme is protein kinase C, the recognition site inserted should preferably contain the motif XRXXSXRX (SEQ ID NO: 35), S being the phosphorylated amino acid. In successful constructs of this type, phosphorylation of the modified GFP may result in detectably altered optical proterties of GFP. It should be noted that extensive deletion may result in loss of the fluorescent propterties of GFP. It has been shown, that only one residue can be sacrificed from the amino terminus and less than 10 or 15 from the carboxyl terminus before fluroescence is lost, cf. Cubitt et al. *TIBS Vol.* 20 (11), pp. 448–456, November 1995. Thus, according to this invention the modification of the GFP gene so as to code for a variant GFP in which one or more amino acid residues have been substituted, inserted or deleted is limited to modifications resulting in a variant GFP having fluorescence properties.

The binding domain of a second messenger may be a receptor of a second messenger. The second messenger may be cyclic AMP, inositol phosphate 3, cyclic GMP, cyclic ADP or diacylglycerol. The binding domain is preferably the cyclic AMP receptor (CRP, e.g. as described in Weber and Steitz, *J. Mol. Biol.* 198, 1987, pp. 311–326; Schroeder and Dobrogosz, *J. Bacteriol.* 167, 1986, pp. 612–622) or a part thereof capable of binding cyclic AMP.

Native CRP has two distinct domains: an N-terminal cAMP binding domain as well as a C-terminal DNA binding activity (Wever and Steitz, *J. Mol. Biol.,* 198 (1987), 311–326). Upon binding of cAMP to the N-terminal portion of CRP a conformational change is induced in the C-terminus, which allows the binding of CRP to the promoter of certain genes. In the successful fusions of CRP (or a portion thereof) to GFP (or a portion thereof), cAMP induced conformational changes in CRP are transmitted to GFP, thereby changing the optical properties of GFP.

In a preferred embodiment of the present invention, the gene or cDNA sequence encoding a wild-type GFP is derived from the jellyfish *Aequorea victoria*. A preferred sequence of this gene is disclosed by FIG. 4a herein. FIG. 4a shows the nucleotide sequence of a wild-type GFP (Hind3-EcoR1 fragment) SEQ ID NO: 30 and FIG. 4b shows the amino acid sequence, wherein start codon ATG corresponds to position 8 and stop codon TAA corresponds to position 722 in the nucleotide sequence of FIG. 4a. SEQ ID NO: 32 . Another sequence of an isotype of this gene is disclosed by Prasher et al., *Gene* 111, 1992, pp. 229–233 (GenBank Accession No. M62653). Any gene that codes for a fluorescent protein, such as wild-type GFP, having a protein kinase recognition site, and derived from any organism expressing a green fluorescent protein of similar fluorescent, phosphorescent or luminescent protein may be used in this invention.

The enzyme recognition site or protein kinase recognition site is preferably a Ser/Thr or Tyr protein kinase, such as protein kinase C or a protein kinase A recognition site (both are reviewd in e.g. B. E. Kemp and R. B. Pearson, *TIBS* 15, September 1990, pp. 342–346), or the insulin receptor or the Src kinase or a portion thereof containing a motif required as a substrate for protein kinase, as suggested above. Kinase catalysed phosphorylation may result in detectably altered optical properties of GFP.

The DNA sequence encoding GFP, the binding domain of a second messenger or the enzyme recognition site may suitably be of genomic or cDNA origin, for instance obtained by preparing a suitable genomic or cDNA library and screening for DNA sequences coding for all or part of any of these proteins by hybridization using synthetic oligonucleotide probes in accordance with standard techniques (cf. Sambrook et al., supra).

The DNA construct of the invention encoding the wild-type GFP, modified GFP or hybrid polypeptide may also be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. According to the phosphoamidite method, oligonucleotides are synthesized, e.g. in an automatic DNA synthesizer, purified, annealed, ligated an cloned in suitable vectors. For most purposes, it may be practical to prepare a shorter DNA sequence such as the DNA sequence coding for the enzyme recognition site synthetically, while the DNA coding for GFP or the binding domain of a second messenger will typically be isolated by screening of a DNA library.

Furthermore, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques (cf. Sambrook et al., *Molecular Cloning: A Laboratory Manual*, 1989, Cold Spring Harbor Laboratory, New York, U.S.A.).

The DNA construct may also be prepared by polymerase chain reaction (PCR) using specific primers, for instance as described in U.S. Pat. No. 4,683,202 or Saiki et al., *Science* 239 (1988), 487–491. A more recent review of PCR methods may be found in *PCR Protocols*, 1990, Academic Press, San Diego, Calif. U.S.A.

The DNA sequence coding for GFP may also be modified by other means such as by conventional chemical mutagenesis or by insertion, deletion or substitution of one or more nucleotides in the sequence, either as random or site-directed mutagenesis. It is expected that such mutants will exhibit altered optical properties or altered heat stability.

The DNA construct of the invention may be inserted into a recombinant vector which may be any vector which may conveniently be subjected to recombinant DNA procedures. The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding wild-type GFP, the modified GFP or the hybrid polypeptide is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the modified GFP or hybrid polypeptide The promoter may be any DNA sequence which shows transcriptional activity in the host cell of choice and may be derived from genes encoding proteins either homologous or heterologous to the host cell.

Examples of suitable promoters for directing the transcription of the DNA sequence encoding wild-type GFP, the modified GFP or hybrid polypeptide in mammalian cells are the SV40 promoter (Subramani et al., *Mol. Cell Biol.* 1 (1981), 854–864), the MT-1 (metallothionein gene) promoter (Palmiter et al., *Science* 222 (1983), 809–814) or the adenovirus 2 major late promoter.

An example of a suitable promoter for use in insect cells is the polyhedrin promoter (U.S. Pat. No. 4,745,051: Vasuvedan et al., *FEBS Lett.* 311, (1992) 7–11), the P10 promoter (J. M. Vlak et al., *J. Gen. Virology* 69, 1988, pp. 765–776), the *Autographa californica* plolyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

Examples of suitable promoters for use in yeast host cells include promoters from yeast glycolytic genes (Hitzeman et al., *J. Biol. Chem.* 255 (1980), 12073–12080; Alber and Kawasaki, *J. Mol. Appl. Gen.* 1 (1982), 419–434) or alcohol dehydrogenase genes (Yound et al., in *Genetic Engineering of Microorganisms for Chemicals* (Hollaender et al, eds.), Plenum Press, New York 1982), or the TPI1 (U.S. Pat. No. 4,599,311) or ADH2-4c (Russell et al., *Nature* 304 (1983), 652–654) promoters.

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *A. oryzae* TAKA amylase; *Rhizomucor miehei* aspartic proteinase, *A. niger* neutral β-amylase, *A. niger* acid stable β-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtillis* alkaline protease gen. or the *Bacillus pumilus* xylosidase gene, or by the phage Lambda $P_R$ or $P_L$ promoters or the *E. coli* lac, trp or tac promoters.

The DNA sequence encoding wild-type GFP, the modified GFP or hybrid polypeptide of the invention may also, if necessary, be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RN As).

The recombinant vector may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid 2 μ replication genes REP 1–3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130), or one which confers resistance to a drug, e.g. ampicillin, kanamycin, tetracyclin, chloramphenicol, neomycin or hygromycin. For filamentous fungi, selectable markers include amdS, pyrG, argB, niaD, sC.

The procedures used to ligate the DNA sequences coding for wild-type GFP, the modified GFP or hybrid polypeptide, the promoter and optionally the terminator and/or secretory signal sequence, respectively, and to insert them into suitable vectors containing the information necessary for repliccation, are well known to persons skilled in the art (cf., for instance, Sambrook et al., op. cit.).

The host cell into which the DNA construct or the recombinant vector of the invention is introduced may be any cell which is capable of expressing the present DNA construct and includes bacteria, yeast, fungi and higher eukaryotic cells, such as mammalian cells.

Examples of bacterial host cells which, on cultivation, are capable of expressing the DNA construct of the invention are grampositive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of *Streptomyces*, such as *S. lividans* or *S. murinvus*, or gramnegative bacteria such as *Echerichia coli*. The trasformation of the bacteria may be effected by protoplast transformation or by using competent cells in a manner known per se (cf. Sambrook et al., supra).

Examples of suitable mammalian cell lines are the HEK293 and the HeLa cell lines, primary cells, and the COS (e.g. ATCC CRL 1650), BHK (e.g. ATCC CRL 1632, ATCC CCL 10), CHL (e.g. ATCC CCL39) or CHO (e.g. ATCC CCL 61) cell lines. Methods of transfecting mammalian cells and expressing DNA sequences introduced in the cells are described in e.g. Kaufman and Sharp, *J. Mol. Biol.* 159 (1982), 601–621; Southern and Berg, *J. Mol. Appl. Genet.* 1 (1982), 327–341; Loyter et al., *Proc. Natl. Acad. Sci. U.S.A.* 79 (1982), 422–426; Wigler et al., *Cell* 14 (1978), 725; Corsaro and Pearson, *Somatic Cell Genetics* 7 (1981), 603; Graham and van der Eb, *Virology* 52 (1973), 456; and Neumann et al., *EMBO J.* 1 (1982), 841–845.

Examples of suitable years cells include cells of Saccharomyces spp. or Schizosaccharomyces spp., in particular strains of *Saccharomyces cerevisiae* or *Saccharomyces kluyveri*. Methods for transforming yeast cells with heterologous DNA and producing heterologous polypeptides therefrom are described, e.g. in U.S. Pat. No. 4,599,311, U.S. Pat. No. 4,931,373, U.S. Pat. No. 4,870,008, U.S. Pat. No. 5,037,743, U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the modified GFP or hybrid polypeptide may be preceded by a signal sequence and optionally a leader sequence, e.g. as described above. Further examples of suitable yeast cells are strains of *Kluyveromyces*, such as *K. lactis, Hansenula*, e.g. *H. polymorpha*, or *Pichia*, e.g. *P. pastoris* (cf. Gleeson et al., *J. Gen. Microbiol.* 132, 1986 pp. 3459–3465; U.S. Pat. No. 4,882,279).

Examples of other fungal cells are cells of filamentous fungi, e.g. Aspergillus spp., Neurospora spp., Fusarium spp. or Trichoderma spp., in particular strains of *A. oryzae, A. nidulans* or *A. niger*. The use of Aspergillus spp. for the expression of proteins is described in, e.g. EP 272 277, EP 230 023, EP 184 438.

When a filamentous fungus is used at the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptide therein may be performed as described in U.S. Pat. No. 4,745,051; U.S. Pat. No. 4,879,236; U.S. Pat. Nos. 5,155,037; 5,162,222; EP 397,485) all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting the expression of the present DNA construct after which the cells may be used in the screening method of the invention. Alternatively, the cells may be disrupted after which cell extracts and/or supernants may be analysed for fluorescence.

The medium used to culture the cells may be any conventional medium suitable for growing the host cells, such as minimal or complex media containing appropriate supplements. Suitable media are available from commerical suppliers or may be prepared according to published recipes (e.g. in catalogues of the American Type Culture Collection).

In the method of the invention, the fluorescence of cells transformed or transfected with the DNA construct of the invention may suitably be measured in a spectrometer where the spectral properties of the cells in liquid culture may be determined as scans of light excitation and emission. Alternatively, such cells grown on nitrocellulose filters placed on plates containing solid media may be illuminated with a scanning polychromatic light source an imaged with an integrating colour camera. The colour of the emitted light may then be determined by image analysis using specialised software.

EXAMPLE 1

Cloning of cDNA Encoding the Green Fluorescent Protein

Briefly, total RNA, isolated from *A. victoria* by a standard procedure (Sambrook et al., *Molecular Cloning*, 2., eds. (1989) (Cold Spring Harbor Laboratory Press: Cold Spring Harbor, N.Y.), 7.19–7.22) was converted into cDNA by using the AMV reverse transcriptase (Promega, Madison, Wis., U.S.A.) as recommended by the manufacturer. The cDNA was then PCR amplified, using PCR primers designed on the basis of a previously published GFP sequence (Prasher et al., *Gene* 111 (1992), 229–233; GenBank accession No. M62653) together with the UITma™ polymerase (Perkin Elmer, Foster City, Calif. U.S.A.). The sequences of the primers were; GFP2: TGGAATAAGCTT- TATGAGTAAAGGAGAAGAACTTTT (SEQ ID NO:1) and GFP-1: AAGAATTCGGATCCCTTTAGTGTCAAT-TGGAAGTCT (SEQ ID NO: 2)

Restriction endonuclease sites inserted in the 5' (a HindIII site) and 3' (EcoRI and BamHI sites) primers facilitated the cloning of the PCR amplified GFP cDNA into a slightly modified pUC19 vector. The details of the construction are as follows: LacZ Shine-Dalgarno AGGA, immediately followed by the 5' HindIII site plus an extra T and the GFP ATG codon, giving the following DNA sequence at the lacZ-promoter GFP fusion point: $P_{LacZ}$-AGGAAAGCTTTATG-GFP (SEQ ID NO: 3). At the 3' end of the GFP cDNA, the base pair corresponding to nucleotide 770 in the published GFP sequence (GenBank accession No. M62653) was fused to the EcoRI site of the pUC19 multiple cloning site (MCS) through a PCR generated BamHI, EcoRI linker region.

EXAMPLE 2

Isolation of Mutant GFPs

A variant of GFP with altered optical properties and/or heat stability is prepared by subjecting the GFP described in Example 1 to a round of chemical mutagenesis followed by screening potential mutants for altered properties.

In brief, the GFP-encoding DNA sequence described in Example 1 (the HindIII-EcoRI fragment) is heat-denatured and subjected to chemical mutagens essentially as described by Myer et al., Science 229, 1985, p. 242. The mutagen is either nitrous acid, or permanganate or formic acid. The resulting mutated population of single stranded GFP fragments are either amplified by PCR using the primers described in Example 1, or reverse transcribed by AMV reverse transcriptase as described in Example 1 prior to amplification by PCR. The PCR products are cleaved by restriction enzymes HindIII and EcoRI and the products of this reaction are ligated into the modified pUC19 plasmid described in Example 1.

The ligation reaction is transformed into an *E. coli* strain and plated on LB agar plates containing 100 µg/ml ampicillin to give approximately 500 transformants per plate. The fluorescence of GFP in the cells is detected by exciting the plates with a light source at 398 nm or 365 nm. Replicas of colonies are made onto fresh plates or plates on which a nitrocellulose filter has been placed prior to replication. When colonies have formed once more, they are individually collected and resuspended in water. The cell suspensions are placed in a LS50B Luminescence Spectrometer (Perkin Elmer Ltd., Beaconsfield, Buckinghamshire, England) equipped with a temperature-controlled cuvet holder, and the spectral properties (scans of both light excitation and emission) are determined. Alternatively, whole plates with approximately 500 transformants are illuminated with a scanning polychromatic light source (fast monochromator from T.I.L.L. (Phototonics, Munich, Germany and imaged with an integrating RGB colour camera Photonic Science Color Cool View), The actual colour of the emitted light was determined by image analysis using the Spec R4 software (Signal Analytics Corporation, Vienna, Va., U.S.A.).

Heat sensitivity of the mutated GFP is tested by characterizing its spectral properties, as described above, after a sequential rise of the temperature from 20° C. to 80° C.

In another round of mutagenesis, *E. coli* cells containing the GFP pUC19 plasmid described in Example 1, are subjected to treatment with N-methyl-N-nitro-N-nitrosoguanidine at a concentration of 25 milligrams per liter for 18 hours, and the cells are plated and analyzed as described above. Alternatively, plasmids are first recovered from the treated cells and transformed into *E. coli* and plated and analyzed as described above.

EXAMPLE 3

Construction of a GFP-Based Recombinant cAMP Probe

The basis of the GFP-based recombinant cAMP probe described herein is the fusion of a portion of the cAMP receptor protein (CRP) from *E. coli* to GFP.

It was decided to prepare 4 basic GFP-CRP fusion constructs, from which a whole array of semi-random fusion constructs may be generated, some of which are expected to have the ability to induce conformational charges in GFP when cAMP is bound to the N-terminal portion of CRP resulting in detectable changes in the optical properties of GFP.

1. Description of the four basic GFP-CRP fusions

Figure 2A:
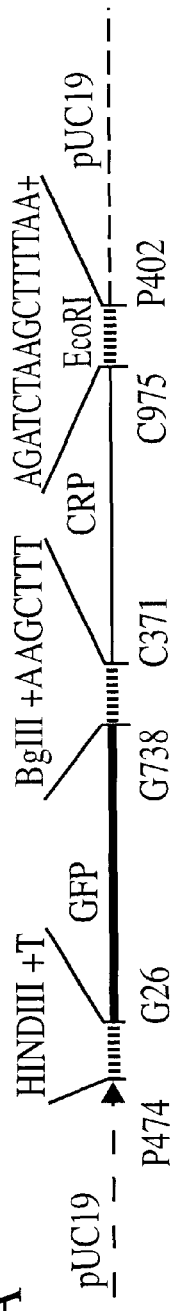
FIG. 2 shows maps of the four basic GFP-CRP fusion contructs:
A) Full length GFP at the N-terminal fused with full length CRP at the C-terminal.
B) Truncated GFP at the N-terminal fused with full length CRP at the C-terminal.
C) Full length CRP at the N-terminal fused with full length GFP at the C-terminal.
D) Truncated CRP at the N-terminal fused with full length GFP at the C-terminal. corresponding to the construct where the DNA binding domain of CRP has been replaced with GFP.

The plasmid harbouring the GFP-CRP fusion shown in FIG. 2A) was constructed the following way: The CRP insert of plasmid pHA7 (Aiba et al., Nucl. acids Res. 10 (1982) 1345–1377) was PCR amplified with the PCR primers CRP1 (CGATACAGATCTAAGCTTTATGGTGCTTGGCAAA CCGC) (SEQ ID NO: 4) and CRP-2 (CGGAATTCTTAAAAGCTTAGATCTTTACCGTGTG CGGAGATCAG) (SEQ ID NO: 5) followed by digestion with the restriction endonucleases BglII and EcoRI (SEQ ID NO: 29). The GFP insert of plasmid pUC19-GFP (see Example 1) was PCR amplified using the PCR primers GFP2 (see Example 1) and GFP-4 (GAATCGTAGATCTTTGTATAGTTCATCCATGCCATG) (SEQ ID NO: 6) followed by digestion with the restriction endonucleases HindIII and BglII. Subsequently, in a three-part ligation, the BglII/EcoRI fragment of the PCR amplified CRP DNA and the HindIII/BglII fragment of the PCR amplified GFP DNA was ligated with a HindIII/EcoRI vector fragment of the slightly modified pUC19 plasmid described in Example 1, followed by transformation of *E. coli*.

Figure 2B:
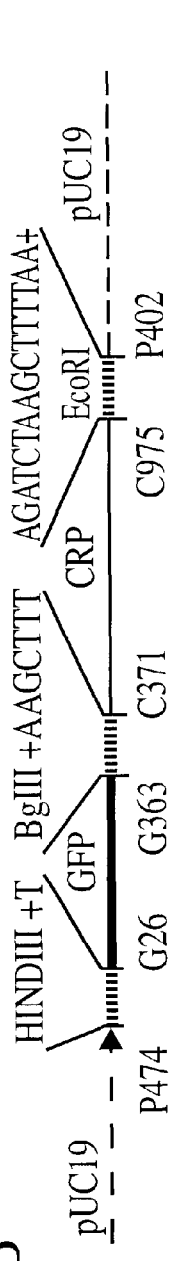

The plasmid harbouring the GFP-CRP fusion shown in FIG. 2B) was constructed essentially as described above for the FIG. 2A) plasmid with a single modification: The PCR primer GFP-3 (GAATCGTAGATCTTTGACTTCAGCACGTGTCTT GTA) (SEQ ID NO: 7) was used instead of the GFP-4 PCR primer.

Figure 2C:
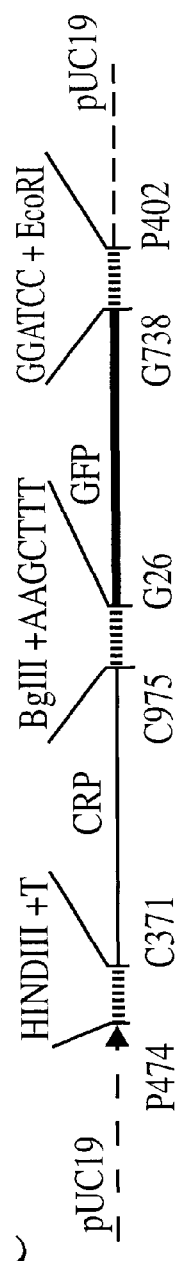

The plasmid harbouring the CRP-GFP fusion shown in FIG. 2C) was made by PCR amplification of the CRP insert of plasmid pHA7 with PCR primers CRP1 and CRP-2, followed by digestion with restriction endonuclease HindIII and ligation into the HindIII site of plasmid pUC19-GFP (see Example 1).

Figure 2D:
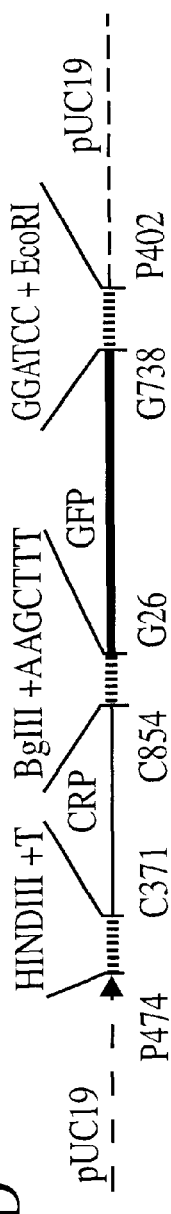

The plasmid harbouring the GFP-CRP fusion shown in FIG. 2D) was constructed essentially as described above for the FIG. 2C) plasmid with a single modification: The PCR primer GFP-1 (CCAGTTAAGCTTAGATCTTCCGGGTGAGTCATAG CGTCTGG) (SEQ ID NO: 8) was used instead of the CRP-2 PCR primer.

2. Generation of semirandom GFP-CRP fusions

The 4 basic GFP-CRP fusion plasmids described above are digested with the restriction endonuclease BglII (opening the plasmids at GFP-CRP fusion points), followed by treatment with the double stranded exonuclease Bal31 for 1 minute, 2 minutes, 3 minutes etc. up to 20 minutes (cf. Sambrook et al., op. cit. at 15.24). Subsequently, the Bal31 treated DNA is incubated with the T4 DNA polymerase (cf. Sambrook et al., op. cit. at 15.24) to generate blunt ends, followed by self ligation (essentially as described by Sambrook et al., op. cit. at 1.68). Finally, the self ligated Bal31 treated plasmid DNA is transformed into E. coli.

3a. Screening of the CRP-GFP fusions for cAMP induced changes in fluorescence

E. coli transformants expressing one of the four basic CRP-GFP fusions or one of the semirandom GFP-CRP fusions are grown overnight in 2 ml Luria-Bertani medium with added ampicillin (100 µg/ml). The cells are then pelleted by centrifugation followed by resuspension in 0.5 ml lysis buffer (100 mM NaCl, 1 mM EDTA and 50 mM Tris pH 8.0). Subsequently, 25 µl 10 mg/ml Lysozyme is added to the resuspended cells, followed by incubation for 10 min. at room temperature, vigorous vortexing and centrifugation for 5 min. at 20,000 x g. Finally, emission and excitation spectra for the resulting protein extracts (the supernatants) are acquired by using the LS50B Luminescence Spectrometer and the FL Data Manager software package (both from Perkin Elmer Ltd., Beaconsfield, Buckinghamshire, England). The spectra recorded before as well as after the addition of cAMP to a final concentration of 0.5 mM are compared by using the Graph Builder software package (Perkin Elmer). The CRP-GFP fusions exhibiting cAMP induced changes in fluorescence are investigated further by expression in mammalian cells.

3b. (alternative protocol) Screening of the CRP-GFP fusions for cAMP induced changes in fluorescence.

Cyclic AMP levels in E. coli cells vary according to the carbon source provided; see e.g. Epstein et.al. (1975), Proc. Natl. Acad. Sci. USA 72, pp. 2300–2304, and Botsford and Harman (1992), Microbiological Reviews 56, p. 100–122. For example, cells grown on glucose contain a lower level of cAMP than cells grown on e.g. glycerol. Furthermore, shifting cells from one carbon source to another, or adding glucose to a culture grown on a non-glucose carbon source change the cAMP level of the cells. Hence, the cAMP-induced change in the fluorescence of the CRP-GFP fusions may be determined by continuously measuring the fluorescence of cells expressing the fusions, after transfer from medium containing e.g. glycerol as carbon to medium containing 0.2% glucose. The cells are analyzed in liquid culture in the LS50B Luminescence Spectrometer or by growing them on nitrocellulose filters placed on plates with solid media; the filter is transferred from plates with one type of medium to plates with another type of medium, and the fluorescence is continuously monitored by exciting the plates with a scanning polychromatic light source (fast monochromator from T.I.L.L. Photonics, Munnich, Germany) and collecting colour images with an integrating RGB color camera (Photonic Science Color Cool View). The actual colour of the emitted light is determined by image analysis using the Spec R4 software package (Signal Analytics Corporation, Vienna, Va., USA).

EXAMPLE 4

Construction of a GFP Based Recombinant Probe for Protein Kinase Activity

Description of the GFP based recombinant protein kinase C (PKC) substrates

Studies on the substrate specificity of the different PKC isoforms using synthetic peptides have shown that peptides containing the motif XRXXSXRX (SEQ ID NO: 35) (S being the phosphorylated amino acid) tend to be the best substrates for PKC (as reviewed in Kemp, B. E. and Pearson, R. B. (1990) TIBS Sep. 15, 342–346). Moreover, the naturally occurring neuronal PKC substrate GAP-43 has the following amino acid sequence around the phosphorylated serine residue (underlined): AATKIQASFRGHIT (SEQ ID NO: 36) (Kosik, K. S. et al. (1988) Neuron 1, 127–132). On the basis of these data we have selected the putative PKC recognition motif RQASFRS (SEQ ID NO: 37) for insertion in GFP at various positions. Insertion points were selected on the basis of surface probability (calculated using the GCG software package, which employs a formula of Emini et al. (1985) J. Virol., 55(3), 836–839), slightly modified for the end values of the protein chains. The single probabilities are taken from Janin et al. (1978) J. Mol. Biol. 125, 357–386) and/or vicinity of the GFP chromophore. The heptapeptide is inserted in GFP by PCR at the following positions: Between amino acid (aa) 39 and aa 40 (PCR primers PKC-1:
GATACCAAAGATCTGAAAGAAGCT-
TGTCGGTATGTTGCATCACCTTCACC (SEQ ID NO: 9) and PKC1: GATACCAAAGATCTGGAAAACTTAC-CCTTAAA
TTT) (SEQ NO: 10), between aa 52 and aa 53 (PCR primers PKC-2:
GATACCAAAGATCTGAAAGAAGCT-
TGTCGTTTTCCAGTAGTGCAAATAAA (SEQ ID NO: 11) and PKC2: GATACCAAAGATCTCTACCTGTTC-CATGGCCAA
CAC) (SEQ ID NO: 12), between aa 71 and aa 72 (PCR primers PKC-3:
GATACCAAAGATCTGAAAGAAGCTTGTC-
GAAAGCATTGAACACCATAAGA (SEQ ID NO: 13) and PKC3: GATACCAAAGATCTTCAAGATACCCA-GATCAT
ATG) (SEQ ID NO: 14), between aa 79 and 80 (PCR primers PKC-4:
GATACCAAAGATCTGAAAGAAGCT-
TGTCGTTTCATATGATCTGGGTATCT (SEQ ID NO: 15) and PKC4: GATACCAAAGATCTCAGCAT-GACTTTTTCAAG
AGT) (SEQ ID NO: 16), between aa 107 and 108 (PCR primers PKC-5:
GATACCAAAGATCTGAAAGAAGCT-
TGTCGCTTGTAGTTCCCGTCATCTTT (SEQ ID NO: 17) and PKC5: GATACCAAAGATCTACACGTGCT-GAAGTCAA
GTTT) (SEQ ID NO 18), between aa 129 and 130 (PCR primers PKC-6:
GATACCAAAGATCTGAAAGAAGCTTGTC-
GATCAATACCTTTTAACTCGAT (SEQ ID NO: 19) and PCK6: GATACCAAAGATCTTTTAAAGAAGATG-GAAA
CATT) (SEQ ID NO: 20), between aa 164 and 165 (PCR primers PKC-7:
GATACCAAAGATCTGAAAGAAGCT-
TGTCGGTTAACTTTGATTCCATTCTT (SEQ ID NO: 21) and PKC7: GATACCAAAGATCTTTCAAAATTA-GACACAAC
ATT) (SEQ ID NO: 22) and between aa 214 and 215 (PCR primers PKC-8:
GATACCAAAGATCTGAAAGAAGCT-
TGTCGCTTTTCGTTGGGATCTTTCGA (SEQ ID NO: 23) and PKC8: GATACCAAAGATCTAGAGACCA-CATGGTCCTT
CTT) (SEQ ID NO: 24).

The PCR primers were designed in the following way: Reverse primers: 5'-GATACCAA AGA TCT GAA AGA AGC TTG TCG-3' (SEQ ID NO: 25)+21 nucleotides of the antisense strand (upstream of the second aa mentioned) and forward primers: 5'-GATACCAA AGA TCT-3+ (SEQ ID NO: 26)+21 nucleotides of the sense strand (downstream of the first aa), each PCR primer being provided with a unique BgIII site (giving rise to the arginine and serine residues of the heptapeptide). The PKC site is inserted by PCR of pUC19-GFP plasmid DNA (see Example 1) with the 8 forward primers and the 8 matching reverse primers, followed by digestion with BgIII, self-ligation and transformation of E. coli (cf. Sambrook et al., op. cit.).

2. Screening of he GFP based recombinant PKC substrates for phosphorylation induced changes in fluorescence E. coli transformants expressing one of the eight GFP based recombinant PKC substrates are grown overnight in 2 ml Luris-Bertani medium with added ampicillin (100 μg/ml). The cells are then pelleted by centrifugation followed by resuspension in 0.5 ml lysis buffer (100 mM NaCl, 1 mM EDTA and 50 mM Tris pH 8.0). Subsequently, 25 μl 10 mg/ml Lysozyme is added to the resuspended cells, followed by incubation for 10 min. at room temperature, vigorous vortexing and centrifugation for 5 min. at 20,000 x g. Finally, emission and excitation spectra for the resulting protein extracts (the supernatants) are acquired by using the LS50B Luminescence Spectrometer and the FL Data Manager software package (Perkin Elmer). The spectra recorded before as well as after treatment of the extracts with purified PKC (Promega, Madison, Wis., USA) according to the manufacturers instruction, are compared by using the Graph Builder software package (Perkin Elmer). The GFP based recombinant PKC substrates exhibiting phosphorylation induced changes in fluorescence are investigated further by expressionin mammalian cells.

EXAMPLE 5

Characterization of the Recombinant Fusion Probes in Mammalian Cells

The CRP-GFP fusions (Example 3) exhibiting cAMP-induced changes in fluorescence as well as the GFP-based recombinant PKC substrates exhibiting phosphorylation-induced changes in fluorescence are investigated further by expression in mammalian cells.

Inserts of the respective plasmids are isolated by digestion with the restriction endonucleases HindIII and BamHI and ligated into the HindIII and BamHI sites of the MCS of the mammalian pREP4 vector (Invitrogen, San Diego, Calif., USA). Subsequently, Baby Hamster Kidney (BHK) are transfected with the resulting plasmid constructs according to the standard calcium phosphate-DNA precipitate protocol (cf. Sambrook et al., op. cit. at 16.33–16.35). Stable transfectants with high expression of the recombinant probes are identified and cloned after 6–14 days in culture by quantifying the fluorescence in an image analysis) system, which consists of a Nikon Diaphot 200 microscope with a temperature controlled stage, a slow scan CCD camera (T.I.L.L. Photonics), a polychromatic light source (T.I.L.L. Photonics), and a PC based image analysis software package (FUCAL from T.I.L.L. Photonics). Alternatively, the fluorescence properties are monitored in a photometer based system. In this system the CCD camera is replaced by a photomultiplier D104 (PTI, Canada).

The clones are cultured for a couple of days in glass coverslip chambers (NUNC, Copenhagen, Denmark) before image analysis.

The ability of the clones to detect changes in cAMP is characterized by elevating intracellular cAMP level by challenging the cells with forskolin (0.1–10 μM) or dibutyryl-cAMP (1–100 μM) and monitoring the associated change of spectral properties. Similarly, clones that are sensitive to variations in PKC activity are characterized by activating PKC in them with PMA (phorbol 12-myristate 13-acetate) (10–1000 nM) or OAG (1-oleoyl-2-acetyl-sn-glycerol) (1–100 μM). The stimulant-induced changes of fluorescence properties are monitored continuously using above mentioned imaging system. Combining imaging with photometry makes it possible to characterize the response of the recombinant probes in both high spatial and high temporal resolution.

EXAMPLE 6

GFP as a Recombinant Probe for Protein Kinase Activity

Purification of GFP from E. coli cells expressing GFP

E. coli cells containing a plasmid allowing expression of GFP were grown overnight at 24° C. Cells were pelleted, the supernatant was discarded, and the pellet was resuspended in ½₀ of the original volume in 100 mM Na-phosphate buffer (pH 8.0). Cells were disrupted by sonication, and cell debris were pelleted at 12000 g for 20 minutes. The supernatant was recovered, ammonium sulphate was added to a final concentration of 1.5 M, and the resulting solution was subjected to hydrophobic interaction chromatography by applying it to a Phenyl-Sepharose CL-4B column equilibrated with 1.5 M ammunium sulphate. The column was eluted with water, and fractions containing GFP were identified by green fluorescence when illuminated with 365 nm UV light. To GFP containing fractions was added one volume of 20 mM Tris, HCl (pH 7.5) and these were subjected to anion exchange chromatography by applying them to a Q-Sepharose column. The column was eluted with 20 mM Tris, HCl (pH 7.5)+1.0 M NaCl. GFP containing fractions were identified by green fluorescence when illuminated with 365 nm UV light. GFP containing fractions were subjected to gelfiltration by applying them to a Superose-12 column equilibrated with 100 mM Na-phosphate buffer (pH 8.0). The column was eluded with 100 mM Na-phosphate buffer (pH 8.0) and fractions containing GFP were identified by green fluorescence when illuminated with 365 nm UV light. The resulting GFP preparation was greater than 95% pure as judged by HPLC analysis.

In vitro GFP phosphorylation assay

For in vitro phosphorylation of GFP, 0.5 μg wild-type GFP (purified as described above) in 40 mM Tris, pH 7.4, 20 mM MgOAc and 0.2 mM ATP (all from Sigma, St. Louis, Mo., USA) was incubated for 1–60 minutes at 37° C. with 0–20 casein units of the catalytic subunit of the cAMP dependent protein kinase (Promega, Madison, Wis. USA) and 0–200 μM cAMP dependent protein kinase inhibitor. Emission (excitation wavelength 395 nm or 470 nm) and excitation (emission wavelength 508 nm) spectra were acquired for all samples using the LS50B Luminescence Spectrometer and the FL data Manager software package (Perkin Elmer). The spectra were subsequently compared by using the Graph Builder software package (Perkin Elmer).

Figure 3:
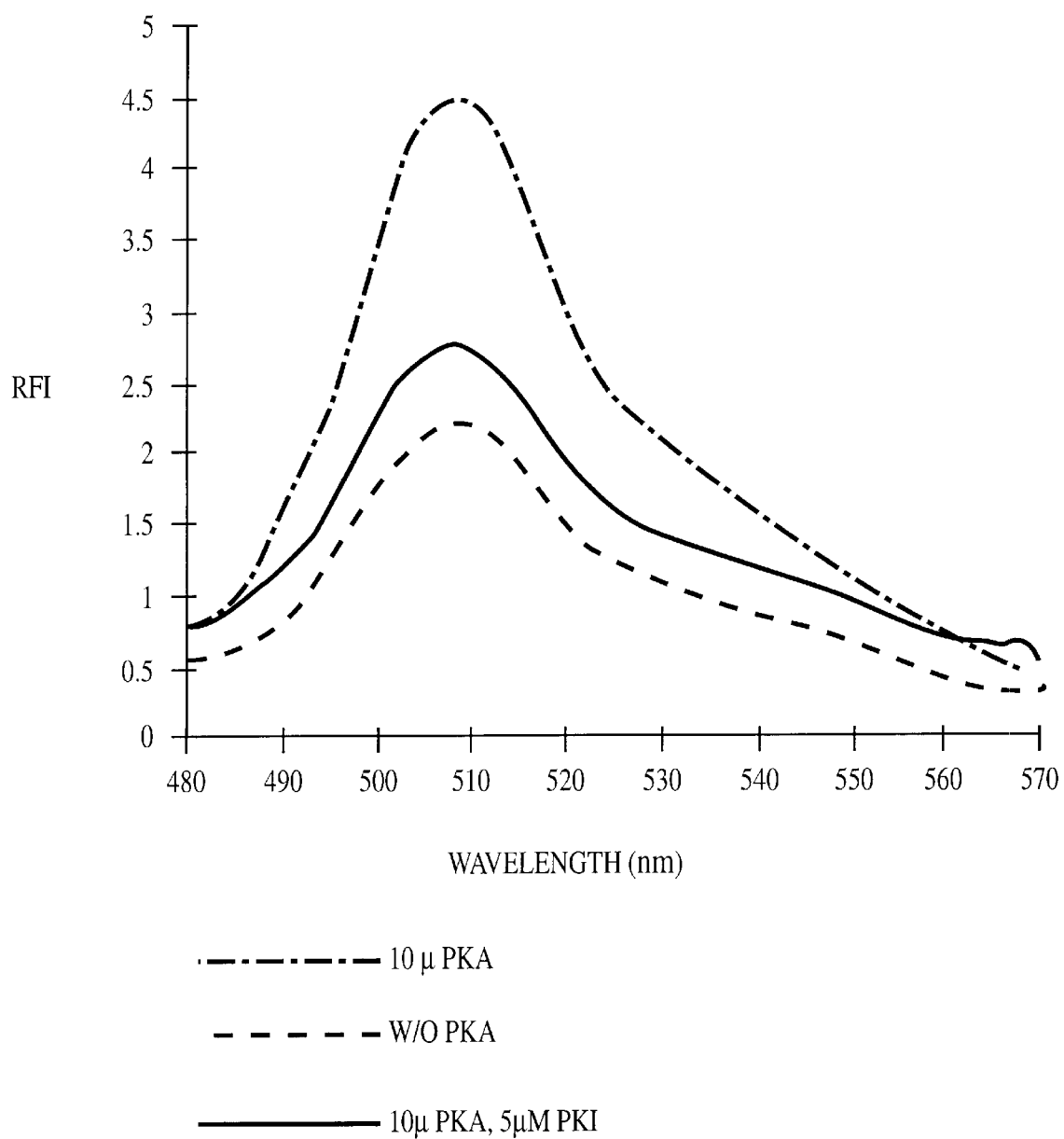
FIG. 3 shows emission spectra of 0.5 μg wild-type GFP (purified as described in Example 6) in 40 mN Tris, pH 7.4, 20 mM MgOAc and 0.2 mM ATP (all forms Sigma), incubated for 5 minuted at 37° C. with 10 casein units of the catalytic subunit of the cAMP dependent protein kinase (Promega) with or without 5 μg cAMP dependent protein kinase inhibitor (PKI).

As can be seen from FIG. 3, the fluorescence intensity of wild-type GFP increases approximately two-fold when incubated with the catalytic subunit of the cAMP dependent protein kinase. Moreover, 5 μm cAMP dependent protein kinase inhibitor inhibits the effect of the catalytic subunit of the cAMP dependent protein kinase.

FIG. 3 shows emission spectra of 0.5 μg wild-type GFP (purified as described in Example 6) in 40 mM Tris, pH 7.4, 20 mM MgOAc and 0.2 mM ATP (all from Sigma), incubated for 5 minutes at 37° C. with 10 casein units of the catalytic subunit of the cAMP dependent protein kinase (Promega) with or without 5 μM cAMP dependent protein kinase inhibitor (PKI). The control (w/o PKA) was incubated 5 minutes at 37° C. without the catalytic subunit of the cAMP dependent protein kinase. The excitation wavelength was 395 nm. RFI in the figure means relative fluorescence intensity.

EXAMPLE 7

Characterization of Wild-type GFP as a PKA Activity Probe in Mammalian Cells The green fluorescent proteins exhibiting phosphorylation-induced changes in fluorescence are investigated further by expression in mammalian cells.

Inserts of the respective plasmids are isolated by digestion with the restriction endonucleases HindIII and BamHI and ligated into the HindIII and BamHI sites of the MCS of the mammalian pZEO-SV vector (Invitrogen, San Diego, Calif., USA). Subsequently, Baby Hamster Kidney (BHK) are transfected with the resulting plasmid constructs according to the standard calcium phosphate-DNA precipitate protocol (cf. Sambrook et al., op. cit. at 16.33–16.35). Stable transfectants with high expression of the recombinant probes are identified and cloned after 6–14 days in culture by quantifying the fluorescence in an image analysis system, which consists of a Nikon Diaphot 200 microscope with a temperature controlled stage, a slow scan CCD camera (T.I.L.L. Photonics), a polychromatic light source (T.I.L.L. Photonics), and a PC based image analysis software package (FUCAL from T.I.L.L. Photonics). Alternatively, the fluorescence properties are monitored in a photometer based system. In this system the CCD camera is replaced by a photomultiplier D104 (PTI, Canada).

The clones are cultured for a couple of days in glass coverslip chambers (NUNC, Copenhagen, Denmark) before image analysis.

The ability of the clones to detect changes in protein kinase A activity is characterized by elevating intracellular cAMP level by challenging the cells with forskolin (0.1–10 $\mu$M) or dibutyryl-cAMP (1–100 $\mu$M) and monitoring the associated change of spectral properties. The stimulant-induced changes of fluorescence properties are monitored continuously using above mentioned imaging system. Combining imaging with photometry makes it possible to characterize the response of the recombinant probes in both high spatial and high temporal resolution.

---

What is claimed is:

1. A method of detecting a biologically active substance affecting intracellular processes mediated through an enzyme or a second messenger, the method comprising:
   (a) culturing a cell containing a DNA sequence, wherein the DNA sequence encodes a Green Fluorescent Protein (GFP) comprising an enzyme recognition site or comprising a binding domain of a second messenger under conditions permitting expression of the DNA sequence;
   (b) measuring the fluorescence of said GFP in the cell in the absence and in the presence of a test sample; and
   (c) comparing the GFP fluorescence measured in step (b); wherein a difference between the fluorescence measured in the absence and in the presence of a test sample indicates the presence in said sample of biologically active substances that affect intracellular processes mediated through the enzyme or the second messenger.

2. The method of claim 1, wherein the cell is a eukaryotic cell.

3. The method of claim 2, wherein the cell is a yeast cell or a mammalian cell.

4. The method of claim 1, wherein the binding domain is a receptor.

5. The method of claim 4, wherein the binding domain is a cyclic AMP receptor that binds cyclic AMP.

6. The method of claim 1, wherein the enzyme recognition site is a protein kinase recognition site.

7. The method of claim 6, wherein the protein kinase recognition site is selected from the group consisting of protein kinase A, protein kinase C, the insulin receptor, and the Src kinase recognition sites.

8. The method of claim 1, wherein the protein or polypeptide is derived from *Aequorea victoria*.

9. The method of claim 1, wherein the DNA sequence encodes a wild-type green fluorescent protein (GFP) having a protein kinase recognition site.

10. The method of claim 1, wherein the DNA sequence is the DNA sequence of SEQ ID NO: 30.

11. A purified DNA sequence comprising a DNA sequence selected from those encoding:
   (a) a modified Green Fluorescent Protein (GFP) comprising an enzyme recognition site;
   (b) a modified GFP comprising a binding domain of a second messenger;
   (c) a hybrid polypeptide comprising wild-type GFP and an attached enzyme recognition site or a binding domain of a second messenger; and
   (d) a hybrid polypeptide comprising modified GFP and an attached enzyme recognition site or a binding domain of a second messenger.

12. The DNA sequence of claim 11, wherein the binding domain is a cyclic AMP receptor that binds cyclic AMP.

13. The DNA sequence of claim 11, wherein the enzyme recognition site is a protein kinase recognition site.

14. The DNA sequence of claim 13, wherein the protein kinase recognition site is selected from the group consisting of protein kinase A, protein kinase C, the insulin receptor, and the Src kinase recognition sites.

15. The DNA sequence of claim 11, wherein the protein or polypeptide sequence is derived from *Aequorea victoria*.

16. The DNA sequence of claim 11, comprising the nucleotide sequence of SEQ ID NO: 30.

17. The cell comprising the DNA sequence of claim 11.

18. A cell of claim 17, wherein the cell is an *Echerichia coli* cell.

19. A cell of claim 18, wherein the cell is an *Exherichia coli*, Accession Number Deutsche Sammlung won Mikrooganismen 10260.

20. A transformation vector comprising the DNA sequence of claim 11.

21. A method of detecting a biologically active substance affecting intracellular processes mediated through a protein kinase or a second messenger, the method comprising:
   (a) culturing a cell containing a DNA sequence, wherein the DNA sequence encodes a protein or polypeptide selected from the group consisting of
      (i) a wild-type green fluorescent protein (GFP) having a protein kinase recognition site;
      (ii) a modified GFP comprising a protein kinase recognition site;
      (iii) a modified GFP comprising a binding domain of a second messenger;
      (iii) a hybrid polypeptide comprising wild-type GFP and an attached protein kinase recognition site or a binding domain of a second messenger; and
      (iv) a hybrid polypeptide comprising modified GFP and an attached protein kinase recognition site or a binding domain of a second messenger;
   under conditions permitting expression of the DNA sequence;
   (b) measuring the fluorescence of the cell of (a);
   (c) incubating the cell with a sample suspected of containing a biologically active substance affecting intracellular processes; and
   (d) measuring the fluorescence of the cell of (c);
   wherein a change in the fluorescence is indicative of the presence of a biologically active substance in said sample.

22. A purified DNA sequence comprising a DNA sequence encoding
   (a) a modified Green Fluorescent Protein (GFP) comprising a protein kinase recognition site;
   (b) a modified GFP comprising a binding domain of a second messenger;
   (c) a hybrid polypeptide comprising wild-type GFP and an attached protein kinase recognition site or a binding domain of a second messenger; and
   (d) a hybrid polypeptide comprising modified GFP and an attached protein kinase recognition site or a binding domain for a second messenger.

23. A method of detecting a biologically active substance affecting intracellular processes mediated through an enzyme, the method comprising:
   (a) culturing a cell containing a DNA sequence, wherein the DNA sequence encodes a Green Fluorescent Protein (GFP) comprising an enzyme recognition site under conditions permitting expression of the DNA sequence;
   (b) measuring the fluorescence of said GFP in the cell in the absence and in the presence of a test sample; and
   (c) comparing the GFP fluorescence measured in step (b); wherein a difference between the fluorescence measured in the absence and in the presence of a test sample indicates the presence in said sample of biologically active substances that affect intracellular processes mediated through the enzyme or the second messenger.

24. A method of detecting a biologically active substance affecting intracellular processes mediated through a second messenger, the method comprising:
   (a) culturing a cell containing a DNA sequence, wherein the DNA sequence encodes a Green Fluorescent Protein (GFP) comprising a binding domain of a second messenger under conditions permitting expression of the DNA sequence;

(b) measuring the fluorescence of said GFP in the cell in the absence and in the presence of a test sample; and (c) comparing the GFP fluorescence measured in step (b); wherein a difference between the fluorescence measured in the absence and in the presence of a test sample indicates the presence in said sample of biologically active substances that affect intracellular processes mediated through the enzyme or the second messenger.

25. The method according to claim 24 or 25, wherein the cell is a eukaryotic cell.

26. The method according to claim 26, wherein the cell is a yeast cell or a mammalian cell.

27. The method according to claim 25, wherein the binding domain is a receptor.

28. The method according to claim 28, wherein the binding domain is a cyclic AMP receptor that binds cyclic AMP.

29. The method according to claim 24, wherein the enzyme recognition site is a protein kinase recognition site.

30. The method according to claim 30, wherein the protein kinase recognition site is selected from the group consisting of protein kinase A, protein kinase C, the insulin receptor, and the Src kinase recognition sites.

31. The method according to claim 24 or 25, wherein the protein or polypeptide is derived from *Aequorea victoria*.

32. The method according to claim 24, wherein the DNA sequence encodes a wild-type green fluorescent protein (GFP) having a protein kinase recognition site.

33. The method according to claim 24 or 25, wherein the DNA sequence is the DNA sequence of SEQ ID NO: 30.

* * * * *

SEQUENCE LISTING

<160> NUMBER OF SEQ ID NOS: 37

<210> SEQ ID NO 1
<211> LENGTH: 36
<212> TYPE: DNA
<213> ORGANISM: Aequorea victoria
<220> FEATURE:

<400> SEQUENCE: 1
tggaataagc tttatgagta aaggagaaga actttt          36

<210> SEQ ID NO 2
<211> LENGTH: 36
<212> TYPE: DNA
<213> ORGANISM: Aequorea victoria

<400> SEQUENCE: 2
aagaattcgg atccctttag tgtcaattgg aagtct          36

<210> SEQ ID NO 3
<211> LENGTH: 14
<212> TYPE: DNA
<213> ORGANISM: Aequorea victoria

<400> SEQUENCE: 3
aggaaagctt tatg                                  14

<210> SEQ ID NO 4
<211> LENGTH: 38
<212> TYPE: DNA
<213> ORGANISM: Aequorea victoria

<400> SEQUENCE: 4
cgatacagat ctaagcttta tggtgcttgg caaaccgc        38

<210> SEQ ID NO 5
<211> LENGTH: 44
<212> TYPE: DNA
<213> ORGANISM: Aequorea victoria

<400> SEQUENCE: 5

-continued cggaattctt aaaagcttag atctttaccg tgtgcggaga tcag        44

<210> SEQ ID NO 6
<211> LENGTH: 36
<212> TYPE: DNA
<213> ORGANISM: Aequorea victoria

<400> SEQUENCE: 6
gaatcgtaga tctttgtata gttcatccat gccatg        36

<210> SEQ ID NO 7
<211> LENGTH: 36
<212> TYPE: DNA
<213> ORGANISM: Aequorea victoria

<400> SEQUENCE: 7
gaatcgtaga tctttgactt cagcacgtgt cttgta        36

<210> SEQ ID NO 8
<211> LENGTH: 41
<212> TYPE: DNA
<213> ORGANISM: Aequorea victoria

<400> SEQUENCE: 8
ccagttaagc ttagatcttc cgggtgagtc atagcgtctg g        41

<210> SEQ ID NO 9
<211> LENGTH: 50
<212> TYPE: DNA
<213> ORGANISM: Aequorea victoria

<400> SEQUENCE: 9
gataccaaag atctgaaaga agcttgtcgg tatgttgcat caccttcacc        50

<210> SEQ ID NO 10
<211> LENGTH: 35
<212> TYPE: DNA
<213> ORGANISM: Aequorea victoria

<400> SEQUENCE: 10
gataccaaag atctggaaaa cttaccctta aattt        35

<210> SEQ ID NO 11
<211> LENGTH: 50
<212> TYPE: DNA
<213> ORGANISM: Aequorea victoria

<400> SEQUENCE: 11
gataccaaag atctgaaaga agcttgtcgt tttccagtag tgcaaataaa        50

<210> SEQ ID NO 12
<211> LENGTH: 36
<212> TYPE: DNA
<213> ORGANISM: Aequorea victoria

<400> SEQUENCE: 12
gataccaaag atctctacct gttccatggc caacac        36

<210> SEQ ID NO 13
<211> LENGTH: 50
<212> TYPE: DNA
<213> ORGANISM: Aequorea victoria

<400> SEQUENCE: 13

-continued gataccaaag atctgaaaga agcttgtcga aagcattgaa caccataaga        50

<210> SEQ ID NO 14
<211> LENGTH: 35
<212> TYPE: DNA
<213> ORGANISM: Aequorea victoria

<400> SEQUENCE: 14
gataccaaag atcttcaaga tacccagatc atatg        35

<210> SEQ ID NO 15
<211> LENGTH: 49
<212> TYPE: DNA
<213> ORGANISM: Aequorea victoria

<400> SEQUENCE: 15
gataccaaag atctgaaaga agcttgtcgt tcatatgat ctgggtatc        49

<210> SEQ ID NO 16
<211> LENGTH: 35
<212> TYPE: DNA
<213> ORGANISM: Aequorea victoria

<400> SEQUENCE: 16
gataccaaag atctcagcat gactttttca agagt        35

<210> SEQ ID NO 17
<211> LENGTH: 50
<212> TYPE: DNA
<213> ORGANISM: Aequorea victoria

<400> SEQUENCE: 17
gataccaaag atctgaaaga agcttgtcgc ttgtagttcc cgtcatcttt        50

<210> SEQ ID NO 18
<211> LENGTH: 35
<212> TYPE: DNA
<213> ORGANISM: Aequorea victoria

<400> SEQUENCE: 18
gataccaaag atctacacgt gctgaagtca agttt        35

<210> SEQ ID NO 19
<211> LENGTH: 49
<212> TYPE: DNA
<213> ORGANISM: Aequorea victoria

<400> SEQUENCE: 19
gataccaaag atctgaaaga agcttgtcga tcaatacctt ttaactcga        49

<210> SEQ ID NO 20
<211> LENGTH: 35
<212> TYPE: DNA
<213> ORGANISM: Aequorea victoria

<400> SEQUENCE: 20
gataccaaag atcttttaaa gaagatggaa acatt        35

<210> SEQ ID NO 21
<211> LENGTH: 49
<212> TYPE: DNA
<213> ORGANISM: Aequorea victoria -continued

```
<210> SEQ ID NO 22
<211> LENGTH: 35
<212> TYPE: DNA
<213> ORGANISM: Aequorea victoria

<400> SEQUENCE: 21
gataccaaag atctgaaaga agcttgtcgg ttaactttga ttccattct          49

<210> SEQ ID NO 22
<211> LENGTH: 35
<212> TYPE: DNA
<213> ORGANISM: Aequorea victoria

<400> SEQUENCE: 22
gataccaaag atctttcaaa attagacaca acatt                         35

<210> SEQ ID NO 23
<211> LENGTH: 50
<212> TYPE: DNA
<213> ORGANISM: Aequorea victoria

<400> SEQUENCE: 23
gataccaaag atctgaaaga agcttgtcgc ttttcgttgg gatctttcga         50

<210> SEQ ID NO 24
<211> LENGTH: 35
<212> TYPE: DNA
<213> ORGANISM: Aequorea victoria

<400> SEQUENCE: 24
gataccaaag atctagagac cacatggtcc ttctt                         35

<210> SEQ ID NO 25
<211> LENGTH: 29
<212> TYPE: DNA
<213> ORGANISM: Aequorea victoria

<400> SEQUENCE: 25
gataccaaag atctgaaaga agcttgtcg                                29

<210> SEQ ID NO 26
<211> LENGTH: 14
<212> TYPE: DNA
<213> ORGANISM: Aequorea victoria

<400> SEQUENCE: 26
gataccaaag atct                                                14

<210> SEQ ID NO 27
<211> LENGTH: 22
<212> TYPE: DNA
<213> ORGANISM: Aequorea victoria

<400> SEQUENCE: 27
cacacaggaa agctttatga gt                                       22

<210> SEQ ID NO 28
<211> LENGTH: 16
<212> TYPE: DNA
<213> ORGANISM: Aequorea victoria

<400> SEQUENCE: 28
aaagggatcc gaattc                                              16

<210> SEQ ID NO 29
<211> LENGTH: 16
<212> TYPE: DNA
<213> ORGANISM: Aequorea victoria
```

<400> SEQUENCE: 29
agatctaagc ttttaa                                                    16

<210> SEQ ID NO 30
<211> LENGTH: 764
<212> TYPE: DNA
<213> ORGANISM: Aequorea victoria

<400> SEQUENCE: 30
aagctttatg agtaaaggag aagaactttt cactggagtt gtcccaattc ttgttgaatt     60
agatggcgat gttaatgggc aaaaattctc tgttagtgga gagggtgaag gtgatgcaac    120
atacggaaaa cttacccctta aatttatttg cactactggg aagctacctg ttccatggcc    180
aacgcttgtc actactttct cttatggtgt tcaatgcttt tcaagatacc cagatcatat    240
gaaacagcat gacttttttca agagtgccat gcccgaaggt tatgtacagg aaagaactat    300
attttacaaa gatgacggga actacaagac acgtgctgaa gtcaagtttg aaggtgatac    360
ccttgttaat agaatcgagt taaaggtat tgattttaaa gaagatggaa acattcttgg    420
acacaaaatg gaatacaact ataactcaca taatgtatac atcatggcag acaaaccaaa    480
gaatggcatc aaagttaact tcaaaattag acacaacatt aaagatggaa gcgttcaatt    540
agcagaccat tatcaacaaa atactccaat tggcgatggc cctgtccttt taccagacaa    600
ccattacctg tccacgcaat ctgccctttc aaagatccc aacgaaaaga gagatcacat    660
gatccttctt gagtttgtaa cagctgctgg gattacacat ggcatggatg aactatacaa    720
ataaatgtcc agacttccaa ttgacactaa agggatccga attc                     764

<210> SEQ ID NO 31
<211> LENGTH: 717
<212> TYPE: DNA
<213> ORGANISM: Aequora victoria
<220> FEATURE:
<221> NAME/KEY: CDS
<222> LOCATION: (1)...(714)

<400> SEQUENCE: 31 atg agt aaa gga gaa gaa ctt ttc act gga gtt gtc cca att ctt gtt      48
Met Ser Lys Gly Glu Glu Leu Phe Thr Gly Val Val Pro Ile Leu Val
 1               5                  10                  15 gaa tta gat ggc gat gtt aat ggg caa aaa ttc tct gtt agt gga gag      96
Glu Leu Asp Gly Asp Val Asn Gly Gln Lys Phe Ser Val Ser Gly Glu
             20                  25                  30 ggt gaa ggt gat gca aca tac gga aaa ctt acc ctt aaa ttt att tgc     144
Gly Glu Gly Asp Ala Thr Tyr Gly Lys Leu Thr Leu Lys Phe Ile Cys
         35                  40                  45 act act ggg aag cta cct gtt cca tgg cca acg ctt gtc act act ttc     192
Thr Thr Gly Lys Leu Pro Val Pro Trp Pro Thr Leu Val Thr Thr Phe
     50                  55                  60 tct tat ggt gtt caa tgc ttt tca aga tac cca gat cat atg aaa cag     240
Ser Tyr Gly Val Gln Cys Phe Ser Arg Tyr Pro Asp His Met Lys Gln
 65                  70                  75                  80 cat gac ttt ttc aag agt gcc atg ccc gaa ggt tat gta cag gaa aga     288
His Asp Phe Phe Lys Ser Ala Met Pro Glu Gly Tyr Val Gln Glu Arg
                 85                  90                  95 act ata ttt tac aaa gat gac ggg aac tac aag aca cgt gct gaa gtc     336
Thr Ile Phe Tyr Lys Asp Asp Gly Asn Tyr Lys Thr Arg Ala Glu Val
             100                 105                 110 aag ttt gaa ggt gat acc ctt gtt aat aga atc gag tta aaa ggt att     384

-continued

```
                Lys Phe Glu Gly Asp Thr Leu Val Asn Arg Ile Glu Leu Lys Gly Ile
                            115                 120                 125 gat ttt aaa gaa gat gga aac att ctt gga cac aaa atg gaa tac aac         432
Asp Phe Lys Glu Asp Gly Asn Ile Leu Gly His Lys Met Glu Tyr Asn
    130                 135                 140 tat aac tca cat aat gta tac atc atg gca gac aaa cca aag aat ggc         480
Tyr Asn Ser His Asn Val Tyr Ile Met Ala Asp Lys Pro Lys Asn Gly
145                 150                 155                 160 atc aaa gtt aac ttc aaa att aga cac aac att aaa gat gga agc gtt         528
Ile Lys Val Asn Phe Lys Ile Arg His Asn Ile Lys Asp Gly Ser Val
                165                 170                 175 caa tta gca gac cat tat caa caa aat act cca att ggc gat ggc cct         576
Gln Leu Ala Asp His Tyr Gln Gln Asn Thr Pro Ile Gly Asp Gly Pro
            180                 185                 190 gtc ctt tta cca gac aac cat tac ctg tcc acg caa tct gcc ctt tcc         624
Val Leu Leu Pro Asp Asn His Tyr Leu Ser Thr Gln Ser Ala Leu Ser
        195                 200                 205 aaa gat ccc aac gaa aag aga gat cac atg atc ctt ctt gag ttt gta         672
Lys Asp Pro Asn Glu Lys Arg Asp His Met Ile Leu Leu Glu Phe Val
    210                 215                 220 aca gct gct ggg att aca cat ggc atg gat gaa cta tac aaa                 714
Thr Ala Ala Gly Ile Thr His Gly Met Asp Glu Leu Tyr Lys
225                 230                 235 taa                                                                     717
```

<210> SEQ ID NO 32
<211> LENGTH: 238
<212> TYPE: PRT
<213> ORGANISM: Aequora victoria

<400> SEQUENCE: 32

```
Met Ser Lys Gly Glu Glu Leu Phe Thr Gly Val Val Pro Ile Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Ala Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205
```

```
Lys Asp Pro Asn Glu Lys Arg Asp His Met Ile Leu Leu Glu Phe Val
    210                 215                 220
Thr Ala Ala Gly Ile Thr His Gly Met Asp Glu Leu Tyr Lys
225                 230                 235
```

<210> SEQ ID NO 33
<211> LENGTH: 5
<212> TYPE: PRT
<213> ORGANISM: Artificial Sequence
<220> FEATURE:
<223> OTHER INFORMATION: Phosphorylation
      Xaa is any amino acid

<400> SEQUENCE: 33

```
Arg Arg Xaa Ser Xaa
1               5
```

<210> SEQ ID NO 34
<211> LENGTH: 8
<212> TYPE: PRT
<213> ORGANISM: Artificial Sequence
<220> FEATURE:
<223> OTHER INFORMATION: Phosphorylation
      Xaa is any amino acid

<400> SEQUENCE: 34

```
Arg Xaa Lys Arg Xaa Xaa Ser Xaa
1               5
```

<210> SEQ ID NO 35
<211> LENGTH: 8
<212> TYPE: PRT
<213> ORGANISM: Artificial Sequence
<220> FEATURE:
<223> OTHER INFORMATION: Phosphorylation
      Xaa is any amino acid

<400> SEQUENCE: 35

```
Xaa Arg Xaa Xaa Ser Xaa Arg Xaa
1               5
```

<210> SEQ ID NO 36
<211> LENGTH: 14
<212> TYPE: PRT
<213> ORGANISM: Artificial Sequence
<220> FEATURE:
<223> OTHER INFORMATION: Phosphorylation

<400> SEQUENCE: 36

```
Ala Ala Thr Lys Ile Gln Ala Ser Phe Arg Gly His Ile Thr
1               5                   10
```

<210> SEQ ID NO 37
<211> LENGTH: 7
<212> TYPE: PRT
<213> ORGANISM: Artificial Sequence
<220> FEATURE:
<223> OTHER INFORMATION: Phosphorylation

<400> SEQUENCE: 37

```
Arg Gln Ala Ser Phe Arg Ser
1               5
```